United States Patent
Johnson et al.

(10) Patent No.: US 10,190,178 B2
(45) Date of Patent: Jan. 29, 2019

(54) **COMPOSITIONS AND METHODS FOR DETECTING MECC-CONTAINING METHICILLIN-RESISTANT *STAPHYLOCOCCUS AUREUS***

(71) Applicant: Roche Molecular Systems, Inc., Pleasanton, CA (US)

(72) Inventors: Jenny A. Johnson, Castro Valley, CA (US); Ashley Hayes, San Francisco, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 15/864,500

(22) Filed: Jan. 8, 2018

(65) Prior Publication Data

US 2018/0148771 A1 May 31, 2018

Related U.S. Application Data

(62) Division of application No. 14/558,220, filed on Dec. 2, 2014, now Pat. No. 9,920,381.

(51) Int. Cl.
*C12Q 1/689* (2018.01)

(52) U.S. Cl.
CPC ........ *C12Q 1/689* (2013.01); *C12Q 2600/112* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 6,001,611 A * | 12/1999 | Will | C07H 21/00 435/6.1 |
| 6,680,370 B1 | 1/2004 | Miyata | |
| 2008/0220428 A1 | 9/2008 | Aichinger et al. | |
| 2013/0266942 A1 | 10/2013 | Menard et al. | |

OTHER PUBLICATIONS

Harrison et al., Antimicrob. Agents Chemother., (2013), 57(3)1524-1528.
Niemeyer, J. Bacteriol., (1996), 178(18)5464-5471.
Paterson, Trends Microbiol., (2014), 22(1)42-47.
Stegger et al., Clin. Microbiol. Infect., (2012), 18(4)395-400.
DTU Food, National Food Institute, 2012, Protocol for PCR Amplification of MEGA, MECC (MECALGA251), SPA and PVL.

* cited by examiner

*Primary Examiner* — Angela M. Bertagna
(74) *Attorney, Agent, or Firm* — David J. Chang

(57) ABSTRACT

Methods for the rapid detection of the presence or absence of mecC-containing *Staphylococcus aureus* (mecC-MRSA) in a biological or non-biological sample are described. The methods can include performing an amplifying step, a hybridizing step, and a detecting step. Furthermore, primers, probes targeting the genes for mecC-MRSA, along with kits are provided that are designed for the detection of mecC-MRSA.

4 Claims, 4 Drawing Sheets

Specification includes a Sequence Listing.

SEQUENCE LISTING

<160> NUMBER OF SEQ ID NOS: 18

<210> SEQ ID NO 1
<211> LENGTH: 31
<212> TYPE: DNA
<213> ORGANISM: Artificial Sequence
<220> FEATURE:
<223> OTHER INFORMATION: Oligonucleotide

<400> SEQUENCE: 1
tcttactatc aaaaagattg ataactctcg c                               31

<210> SEQ ID NO 2
<211> LENGTH: 34
<212> TYPE: DNA
<213> ORGANISM: Artificial Sequence
<220> FEATURE:
<223> OTHER INFORMATION: Oligonucleotide

<400> SEQUENCE: 2
ctcttttagt ttctatgtac tttcttacta tcaa                            34

<210> SEQ ID NO 3
<211> LENGTH: 30
<212> TYPE: DNA
<213> ORGANISM: Artificial Sequence
<220> FEATURE:
<223> OTHER INFORMATION: Oligonucleotide

<400> SEQUENCE: 3
gaatatcaag taacatctca gcaatgatac                                 30

<210> SEQ ID NO 4
<211> LENGTH: 34
<212> TYPE: DNA
<213> ORGANISM: Artificial Sequence
<220> FEATURE:
<223> OTHER INFORMATION: Oligonucleotide

<400> SEQUENCE: 4
atctgtataa aatagattag tcctttattg cgta                            34

<210> SEQ ID NO 5
<211> LENGTH: 29
<212> TYPE: DNA
<213> ORGANISM: Artificial Sequence
<220> FEATURE:
<223> OTHER INFORMATION: Oligonucleotide

<400> SEQUENCE: 5
tagtaagtga ggttgctgaa attgtacta                                  29

<210> SEQ ID NO 6
<211> LENGTH: 28
<212> TYPE: DNA
<213> ORGANISM: Artificial Sequence
<220> FEATURE:
<223> OTHER INFORMATION: Oligonucleotide

<400> SEQUENCE: 6
caattctcat aaacctcata cgtaaaga                                   28

<210> SEQ ID NO 7
<211> LENGTH: 22
<212> TYPE: DNA
<213> ORGANISM: Artificial Sequence

```
<220> FEATURE:
<223> OTHER INFORMATION: Oligonucleotide

<400> SEQUENCE: 7
acggcaattc tcataaacct ca                                              22

<210> SEQ ID NO 8
<211> LENGTH: 21
<212> TYPE: DNA
<213> ORGANISM: Artificial Sequence
<220> FEATURE:
<223> OTHER INFORMATION: Oligonucleotide

<400> SEQUENCE: 8
actctcgcaa aacataacgg c                                               21

<210> SEQ ID NO 9
<211> LENGTH: 27
<212> TYPE: DNA
<213> ORGANISM: Artificial Sequence
<220> FEATURE:
<223> OTHER INFORMATION: Oligonucletoide

<400> SEQUENCE: 9
gaaatacaag gaaagatgct atcttcc                                         27

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide

<400> SEQUENCE: 10
ttgaaccaac gcatgaccca agggc                                           25

<210> SEQ ID NO 11
<211> LENGTH: 339
<212> TYPE: DNA
<213> ORGANISM: Artificial Sequence
<220> FEATURE:
<223> OTHER INFORMATION: Oligonucleotide

<400> SEQUENCE: 11
gaaatacaag gaaagatgct atcttccgaa ggattggccc aagaattgaa ccaacgcatg      60
acccaagggc aaagcgactt tgtattcgtc attggcggat caaatggcct gcacaaggac     120
gtcttacaac gcagtaacta cgcactatca ttcagcaaaa tgacatttcc acatcaaatg     180
atgcgggttg tgttaattga gcaagtgtat agagcgttta agattatgcg cggagaagcg     240
tatcacaaat gatgcggttt ttttaacctc tttacgtatg aggtttatga gaattgccgt     300
tatgttttgc gagagttatc aatcttttg atagtaaga                             339

<210> SEQ ID NO 12
<211> LENGTH: 361
<212> TYPE: DNA
<213> ORGANISM: Artificial Sequence
<220> FEATURE:
<223> OTHER INFORMATION: Oligonucleotide

<400> SEQUENCE: 12
gaaatacaag gaaagatgct atcttccgaa ggattggccc aagaattgaa ccaacgcatg      60
acccaagggc aaagcgactt tgtattcgtc attggcggat caaatggcct gcacaaggac     120
```

```
gtcttacaac gcagtaacta cgcactatca ttcagcaaaa tgacatttcc acatcaaatg    180
atgcgggttg tgttaattga gcaagtgtat agagcgttta agattatgcg cggagaagcg    240
tatcacaaat gatgcggttt ttttaacctc tttacgtatg aggtttatga gaattgccgt    300
tatgttttgc gagagttatc aatcttttg atagtaagaa agtacataga aactaaaaga    360
g                                                                   361

<210> SEQ ID NO 13
<211> LENGTH: 454
<212> TYPE: DNA
<213> ORGANISM: Artificial Sequence
<220> FEATURE:
<223> OTHER INFORMATION: Oligonucleotide

<400> SEQUENCE: 13
gaaatacaag gaaagatgct atcttccgaa ggattggccc aagaattgaa ccaacgcatg     60
acccaagggc aaagcgactt tgtattcgtc attggcggat caaatggcct gcacaaggac    120
gtcttacaac gcagtaacta cgcactatca ttcagcaaaa tgacatttcc acatcaaatg    180
atgcgggttg tgttaattga gcaagtgtat agagcgttta agattatgcg cggagaagcg    240
tatcacaaat gatgcggttt ttttaacctc tttacgtatg aggtttatga gaattgccgt    300
tatgttttgc gagagttatc aatcttttg atagtaagaa agtacataga aactaaaaga    360 gtattttat ctacaatagc atttataatt tattctatta ttgtatactt tattttaatt    420
attagtatca ttgctgagat gttacttgat attc                               454

<210> SEQ ID NO 14
<211> LENGTH: 537
<212> TYPE: DNA
<213> ORGANISM: Artificial Sequence
<220> FEATURE:
<223> OTHER INFORMATION: Oligonucleotide

<400> SEQUENCE: 14
gaaatacaag gaaagatgct atcttccgaa ggattggccc aagaattgaa ccaacgcatg     60
acccaagggc aaagcgactt tgtattcgtc attggcggat caaatggcct gcacaaggac    120
gtcttacaac gcagtaacta cgcactatca ttcagcaaaa tgacatttcc acatcaaatg    180
atgcgggttg tgttaattga gcaagtgtat agagcgttta agattatgcg cggagaagcg    240
tatcacaaat gatgcggttt ttttaacctc tttacgtatg aggtttatga gaattgccgt    300
tatgttttgc gagagttatc aatcttttg atagtaagaa agtacataga aactaaaaga    360 gtattttat ctacaatagc atttataatt tattctatta ttgtatactt tattttaatt    420
attagtatca ttgctgagat gttacttgat attctatgtc tatttttag gaaattctat    480 actattaaaa ttatggtatt ttatacgcaa taaaggacta atctatttta tacagat      537

<210> SEQ ID NO 15
<211> LENGTH: 614
<212> TYPE: DNA
<213> ORGANISM: Artificial Sequence
<220> FEATURE:
<223> OTHER INFORMATION: Oligonucleotide

<400> SEQUENCE: 15
gaaatacaag gaaagatgct atcttccgaa ggattggccc aagaattgaa ccaacgcatg     60
acccaagggc aaagcgactt tgtattcgtc attggcggat caaatggcct gcacaaggac    120
gtcttacaac gcagtaacta cgcactatca ttcagcaaaa tgacatttcc acatcaaatg    180
```

```
atgcgggttg tgttaattga gcaagtgtat agagcgttta agattatgcg cggagaagcg    240
tatcacaaat gatgcggttt ttttaacctc tttacgtatg aggtttatga gaattgccgt    300
tatgttttgc gagagttatc aatcttttg atagtaagaa agtacataga aactaaaaga    360
gtatttttat ctacaatagc atttataatt tattctatta ttgtatactt tattttaatt    420
attagtatca ttgctgagat gttacttgat attctatgtc tattttttag gaaattctat    480
actattaaaa ttatggtatt ttatacgcaa taaaggacta atctatttta tacagattag    540
tcctttattg tagtctttaa aaactagtta ctcattaata ttttttagta caatttcagc    600
aacctcactt acta                                                      614
```

<210> SEQ ID NO 16
<211> LENGTH: 339
<212> TYPE: DNA
<213> ORGANISM: Artificial Sequence
<220> FEATURE:
<223> OTHER INFORMATION: Oligonucleotide

<400> SEQUENCE: 16

```
gaaatacaag gaaagatgct atcttccgaa ggattggccc aagaattgaa ccaacgcatg     60
acccaagggc aaagcgactt tgtattcgtc attggcggat caaatggcct gcacaaggac    120
gtcttacaac gcagtaacta cgcactatca ttcagcaaaa tgacatttcc acatcaaatg    180
atgcgggttg tgttaattga gcaagtgtat agagcgttta agattatgcg cggagaagcg    240
tatcacaaat gatgcggttt ttttaacctc tttacgtatg aggtttatga gaattgccgt    300
tatgttttgc gagagttatc aatcttttg atagtaaga                            339
```

<210> SEQ ID NO 17
<211> LENGTH: 300
<212> TYPE: DNA
<213> ORGANISM: Artificial Sequence
<220> FEATURE:
<223> OTHER INFORMATION: Oligonucleotide

<400> SEQUENCE: 17

```
gaaatacaag gaaagatgct atcttccgaa ggattggccc aagaattgaa ccaacgcatg     60
acccaagggc aaagcgactt tgtattcgtc attggcggat caaatggcct gcacaaggac    120
gtcttacaac gcagtaacta cgcactatca ttcagcaaaa tgacatttcc acatcaaatg    180
atgcgggttg tgttaattga gcaagtgtat agagcgttta agattatgcg cggagaagcg    240
tatcacaaat gatgcggttt ttttaacctc tttacgtatg aggtttatga gaattgccgt    300
```

<210> SEQ ID NO 18
<211> LENGTH: 316
<212> TYPE: DNA
<213> ORGANISM: Artificial Sequence
<220> FEATURE:
<223> OTHER INFORMATION: Oligonucleotide

<400> SEQUENCE: 18

```
gaaatacaag gaaagatgct atcttccgaa ggattggccc aagaattgaa ccaacgcatg     60
acccaagggc aaagcgactt tgtattcgtc attggcggat caaatggcct gcacaaggac    120
gtcttacaac gcagtaacta cgcactatca ttcagcaaaa tgacatttcc acatcaaatg    180
atgcgggttg tgttaattga gcaagtgtat agagcgttta agattatgcg cggagaagcg    240
```

```
tatcacaaat gatgcggttt ttttaacctc tttacgtatg aggtttatga gaattgccgt    300
tatgttttgc gagagt                                                    316
```

COMPOSITIONS AND METHODS FOR DETECTING MECC-CONTAINING METHICILLIN-RESISTANT *STAPHYLOCOCCUS AUREUS*

CROSS REFERENCE TO RELATED APPLICATIONS

This application is a divisional of U.S. patent application Ser. No. 14/558,220, filed on Dec. 2, 2014, now issued as U.S. Pat. No. 9,920,381, the content of which is incorporated by reference herein in its entirety.

FIELD OF THE INVENTION

The present disclosure relates to the field of bacterial diagnostics, and more particularly to detection of methicillin-resistant *Staphylococcus aureus* (MRSA) that contain mecC nucleic acid sequences.

BACKGROUND OF THE INVENTION

*Staphylococcus aureus* ("*S. aureus*" or "SA") is a facultative anaerobic, Gram-positive bacterium, whose natural reservoir includes the human skin and nose and can also inhabit wounds. Most people who carry *S. aureus* show no sign of infection; however, *S. aureus* can become invasive and cause infection in the body if the normal barrier is breached. *S. aureus* can cause a number of illnesses ranging from minor skin infections such as pimples, boils, and abscesses, to major diseases such as pneumonia, meningitis, and sepsis. Tissues other than skin and nose can be infected when barriers are breached, e.g., skin or mucosal lining, which leads to furuncles and carbuncles. *S. aureus* infections can spread between people through skin contact with an infected person or contact with objects used by an infected person.

*S. aureus* possess a remarkable ability to develop resistance to the major antibiotics, including the penicillins (methicillin, oxacillin, cloxacillin and flucloxacillin), which has earned it the label "superbug". Methicillin-resistant *S. aureus* (MRSA) is a bacterium that has become resistant to penicillins, and it is responsible for several human infections that are difficult to treat. MRSA may also be known as oxacillin-resistant *S. aureus* (ORSA) and multiple-resistant *S. aureus*, while the non-methicillin resistant strains of *S. aureus* are sometimes called methicillin-sensitive *S. aureus* (MSSA).

The gene required for methicillin resistance in staphylococci, mecA, encodes the low-affinity penicillin-binding protein 2a (PBP2a) (Niemeyer et al., J. Bacteriol., (1996), 178(18):5464-5471). A novel variant of mecA (mecA$_{LGA251}$), which has been renamed as mecC, was recently identified in *S. aureus* isolates from both humans and animals (Harrison et al., Antimicrob. Agents Chemother., (2013), 57(3):1524-1528). This homologue shares 70% nucleotide identity with the mecA gene, and its presence poses diagnostic problems with the potential to be misdiagnosed as methicillin-sensitive *S. aureus* (Paterson et al., Trends Microbiol., (2014), 22(1):42-47). Thus there is a need in the art for a quick and reliable method to specifically detect mecC-containing MRSA in a sensitive manner.

SUMMARY OF THE INVENTION

Certain embodiments in the present disclosure relate to methods for the rapid detection of the presence or absence of mecC-containing *Staphylococcus aureus* (mecC-MRSA) in a biological or non-biological sample, for example, multiplex detection of mecC-MRSA by real-time polymerase chain reaction in a single test tube. Embodiments include methods of detection of mecC-MRSA comprising performing at least one cycling step, which may include an amplifying step and a hybridizing step. Furthermore, embodiments include primers, probes, and kits that are designed for the detection of mecC-MRSA in a single tube. The detection methods are designed to target the mecC gene which allows one to detect mecC-MRSA in a single test.

In one embodiment, a method for detecting mecC-containing *Staphylococcus aureus* in a sample is provided, including performing an amplifying step including contacting the sample with an orfX primer and a mecC-MRSA primer to produce an amplification product if mecC-MRSA is present in the sample; performing a hybridizing step including contacting the amplification product with one or more detectable mecC-MRSA probes; and detecting the presence or absence of the amplified product, wherein the presence of the amplified product is indicative of the presence of mecC-MRSA in the sample and wherein the absence of the amplified product is indicative of the absence of mecC-MRSA in the sample; wherein the orfX primer comprises or consists of the sequence of SEQ ID NO: 9, or a complement thereof, and the mecC-MRSA primer comprises a sequence selected from the group consisting of SEQ ID NOs: 1, 2, 3, 4, 5, 6, 7, and 8, or a complement thereof; and wherein the detectable mecC-MRSA probe comprises or consists of the sequence of SEQ ID NO: 10, or a complement thereof.

In one embodiment, the primer set for amplification of the mecC-MRSA gene target include nucleic acid sequences of SEQ ID NOs: 1, 2, 3, 4, 5, 6, 7, 8, and 9 or a complement thereof, and the detectable probe for detection of the mecC-MRSA amplification product includes the nucleic acid sequence of SEQ ID NO: 10.

Other embodiments provide an oligonucleotide comprising or consisting of a sequence of nucleotides selected from SEQ ID NOs: 1, 2, 3, 4, 5, 6, 7, 8, 9, and 10, or a complement thereof, which oligonucleotide has 100 or fewer nucleotides. In another embodiment, the present disclosure provides an oligonucleotide that includes a nucleic acid having at least 70% sequence identity (e.g., at least 75%, 80%, 85%, 90% or 95%, etc.) to one of SEQ ID NOs: 1, 2, 3, 4, 5, 6, 7, 8, 9, 10, 11, and 12, or a complement thereof, which oligonucleotide has 100 or fewer nucleotides. Generally, these oligonucleotides may be primer nucleic acids, probe nucleic acids, or the like in these embodiments. In certain of these embodiments, the oligonucleotides have 40 or fewer nucleotides (e.g. 35 or fewer nucleotides, 30 or fewer nucleotides, etc.) In some embodiments, the oligonucleotides comprise at least one modified nucleotide, e.g. to alter nucleic acid hybridization stability relative to unmodified nucleotides. Optionally, the oligonucleotides comprise at least one label and/or at least one quencher moiety. In some embodiments, the oligonucleotides include at least one conservatively modified variation. "Conservatively modified variations" or, simply, "conservative variations" of a particular nucleic acid sequence refers to those nucleic acids, which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

In one aspect, amplification can employ a polymerase enzyme having 5' to 3' nuclease activity. Thus, the first and second fluorescent moieties may be within no more than 8 nucleotides of each other along the length of the probe. In another aspect, the mecC-MRSA probes includes a nucleic acid sequence that permits secondary structure formation. Such secondary structure formation generally results in spatial proximity between the first and second fluorescent moiety. According to this method, the second fluorescent moiety on the probe can be a quencher.

The present disclosure provides for methods of detecting the presence or absence of mecC-MRSA in a biological sample from an individual. Such methods generally include performing at least one cycling step, which includes an amplifying step and a dye-binding step. Typically, the amplifying step includes contacting the sample with a plurality of pairs of mecC-MRSA primers to produce one or more mecC-MRSA amplification products if a mecC-MRSA nucleic acid molecule is present in the sample, and the dye-binding step includes contacting the mecC-MRSA amplification product with a double-stranded DNA binding dye. Such methods also include detecting the presence or absence of binding of the double-stranded DNA binding dye into the amplification product, wherein the presence of binding is indicative of the presence of mecC-MRSA in the sample, and wherein the absence of binding is indicative of the absence of mecC-MRSA in the sample. A representative double-stranded DNA binding dye is ethidium bromide. In addition, such methods also can include determining the melting temperature between the mecC-MRSA amplification product and the double-stranded DNA binding dye, wherein the melting temperature confirms the presence or absence of mecC-MRSA.

In a further embodiment, a kit for detecting one or more nucleic acids of mecC-MRSA is provided. The kit can include a plurality of sets of mecC-MRSA primers specific for amplification of the mecC gene target; and one or more detectable mecC-MRSA probes specific for detection of the mecC-MRSA amplification products.

In one aspect, the kit can include probes already labeled with donor and corresponding acceptor fluorescent moieties, or can include fluorophoric moieties for labeling the probes. The kit can also include nucleoside triphosphates, nucleic acid polymerase, and buffers necessary for the function of the nucleic acid polymerase. The kit can also include a package insert and instructions for using the primers, probes, and fluorophoric moieties to detect the presence or absence of mecC-MRSA in a sample.

Unless otherwise defined, all technical and scientific terms used herein have the same meaning as commonly understood by one of ordinary skill in the art to which this invention belongs. Although methods and materials similar or equivalent to those described herein can be used in the practice or testing of the present subject matter, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION OF THE INVENTION

Figure 1:
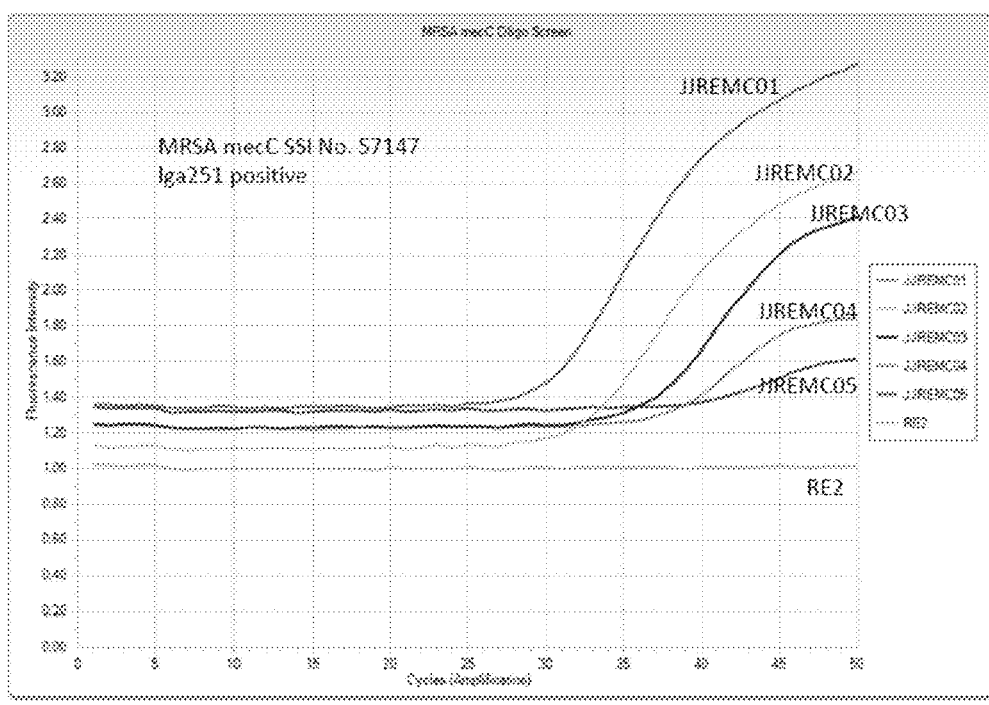
FIG. 1 shows PCR growth curves of experiments using several primers specific for mecC MRSA compared with a primer (RE2) specific for mecA containing MRSA.

Diagnosis of mecC-MRSA infection by nucleic acid amplification provides a method for rapidly and accurately detecting the bacterial infection. A real-time assay for detecting mecC-MRSA in a sample is described herein. Primers and probes for detecting mecC-MRSA are provided, as are articles of manufacture or kits containing such primers and probes. The increased sensitivity of real-time PCR for detection of mecC-MRSA compared to other methods, as well as the improved features of real-time PCR including sample containment and real-time detection of the amplified product, make feasible the implementation of this technology for routine diagnosis of mecC-MRSA infections in the clinical laboratory.

Similar to mecA, the homolog methicillin-resistance gene, mecC, encodes an altered methicillin-resistant penicillin-binding protein (PBP2a or PBP2'), a penicillin binding protein with reduced affinity for β-lactam rings (the primary active-site of the β-lactam antibiotics such as penicillins, cephalosporins and carbapenems) (Guignard et al., 2005, Curr Opin Pharmacol 5 (5): 479-89), that is not present in susceptible strains and is believed to have been acquired from a distantly related species. MecC is carried on a mobile genetic element, the Staphylococcal Chromosomal Cassette mec (SCCmec) of MRSA strains. SCC elements also occur in sensitive *S. aureus* but do not carry the mecC gene or carry a non-functional mecC gene. Such strains can be a source of false positive results, because they may have the same right extremity junction.

However, MRSA detection from nasal specimen by detecting the mecC gene and a *S. aureus* specific gene leads to low positive predictive values (PPV) due to the presence of varying amounts of both non-resistant *S. aureus* and methicillin-resistant coagulase-negative Staphylococci (MRCoNS). A combination of those is undistinguishable from MRSA, because of the presence of both targets. Depending on the prevalence of MRSA this situation leads up to 30% false positive results. For a better PPV, the chosen target needs to be unique for MRSA. The only target currently known is Staphylococcal Chromosomal Cassette (SCCmec), which amplifies the transposon integration site for the genetic element carrying the mecC gene.

SCCmec, the SCC element of MRSA (with functional mecC gene), is a transposon of highly veriable length (16 kb-67 kb) integrated into the 3' portion of the open reading frame X from *S. aureus* (orfX) containing the mecC gene. OrfX has no defined function in *S. aureus* and is unique to *S. aureus*. The integration of SCCmec creates a signature unique to MRSA.

SCCmec elements have two essential components; the ccr gene complex (ccr) and the mec gene complex (mec). The ccr gene complex is composed of ccr genes and surrounding open reading frames (ORFs), and the mec gene complex is composed of the mecC gene, regulatory genes, and insertion sequences upstream or downstream of mecC.

Classification of MRSA can be based on different genotypes of MRSA. One target for MRSA detection and classification based on genotypes may be the right extremity junction (RE) of the SCCmec. This method of MRSA typing relates is therefore called RE (right extremity of SCCmec) typing. This typing method takes advantage of the polymorphism at the right extremity of SCCmec DNAs adjacent to the integration site among the different types of SCCmec.

The detection of mecC-containing *S. aureus* (mecC-MRSA) utilizes a strategy to produce an amplicon at the RE junction between the *S. aureus* orfX gene and SCCmec carrying the mecC gene which confers resistance to methicillin. To accomplish this, one primer is anchored in a highly conserved region of the orfX gene of *S. aureus* (orfX primer), and a second primer is located within the non-conserved RE junction of SCCmec (RE primer or mecC-MRSA primer). The resulting amplicon from the two primers spans part of the orfX gene and part of SCCmec. Due to the non-homologous nature of SCCmec at the RE junction, several different RE primers are necessary in order to accomplish the most coverage of unique MRSA strains carrying mecC genes. In the present disclosure, the specific sequence of the RE region of MRSA carrying mecC was determined for 14 unique mecC strains, and RE primers were designed from those sequences for inclusive detection of the mecC carrying MRSA strains. To detect the resulting amplicons, one or more detectable mecC-MRSA probes may be utilized wherein the mecC-MRSA probes include a sequence that can partially or entirely hybridize to a portion of the amplicon at a location containing the highly conserved region of the orfX gene. The primers can be used in a kit for detection of mecC-MRSA, which can also include a multiplex for inclusive detection of MRSA carrying mecA or mecC genes.

The disclosed methods may include performing at least one cycling step that includes amplifying one or more portions of mecC-MRSA nucleic acid molecule gene target from a sample using one or more pairs of mecC-MRSA primers. "mecC-MRSA primers" as used herein refer to oligonucleotide primers that specifically anneal to nucleic acid sequence encoding mecC in MRSA in the non-conserved RE junction of SCCmec, and initiate DNA synthesis therefrom under appropriate conditions. Each of the discussed mecC-MRSA primers anneals to a target within or adjacent to the respective mecC-MRSA target nucleic acid molecule such that at least a portion of each amplification product contains nucleic acid sequence corresponding to the target. The one or more of mecC amplification products are produced provided that one or more of mecC nucleic acid is present in the sample, thus the presence of the one or more of mecC amplification products is indicative of the presence of mecC-MRSA in the sample. The amplification product should contain the nucleic acid sequences that are complementary to one or more detectable probes for mecC-MRSA. Each cycling step includes an amplification step, a hybridization step, and a detection step, in which the sample is contacted with the one or more detectable probes for mecC-MRSA for detection of the presence or absence of mecC-MRSA in the sample.

As used herein, the term "amplifying" refers to the process of synthesizing nucleic acid molecules that are complementary to one or both strands of a template nucleic acid molecule (e.g., mecC). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" is used herein as known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'-OH group whereto further "nucleotides" may be attached by a template-dependent DNA polymerase establishing 3' to 5' phosphodiester linkage whereby deoxynucleoside triphosphates are used and whereby pyrophosphate is released. Therefore, there is—except possibly for the intended function—no fundamental difference between a "primer", an "oligonucleotide", or a "probe".

The term "hybridizing" refers to the annealing of one or more probes to an amplification product. Hybridization conditions typically include a temperature that is below the melting temperature of the probes but that avoids non-specific hybridization of the probes.

The term "5' to 3' nuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-O-methyl Ribo-U, 2'-O-methyl Ribo-C, an N4-ethyl-dC, an N6-methyl-dA, and the like. Many other modified nucleotides that can be substituted in the oligonucleotides are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments. Examples of these types of nucleic acid modifications are described in, e.g., U.S. Pat. No. 6,001,611, which is incorporated herein by reference.

MecC-Containing *Staphylococcus aureus* (mecC-MRSA)

The present disclosure provides methods to detect mecC-MRSA by amplifying, for example, a portion of the mecC nucleic acid sequence. Nucleic acid sequences of SCCmec of various subtypes of mecC-MRSA are available (e.g., GenBank Accession No. FR823292). Specifically, primers and probes to amplify and detect mecC-MRSA nucleic acid molecule targets are provided by the embodiments in the present disclosure.

For detection of mecC-MRSA, primers and probes to amplify the mecC-MRSA RE junctions are provided. MecC-MRSA nucleic acids other than those exemplified herein can also be used to detect mecC-MRSA in a sample. For example, functional variants can be evaluated for specificity and/or sensitivity by those of skill in the art using routine methods. Representative functional variants can include, e.g., one or more deletions, insertions, and/or substitutions in the mecC-MRSA nucleic acids disclosed herein.

More specifically, embodiments of the oligonucleotides each include a nucleic acid with a sequence selected from SEQ ID NOs: 1, 2, 3, 4, 5, 6, 7, 8, 9, and 10, a substantially identical variant thereof in which the variant has at least, e.g., 80%, 90%, or 95% sequence identity to one of SEQ ID NOs: 1, 2, 3, 4, 5, 6, 7, 8, 9, and 10, or a complement of SEQ ID NOs: 1, 2, 3, 4, 5, 6, 7, 8, 9, and 10 and the variant.

TABLE I

MecC-MRSA Primers and Probe

| SEQ ID NO | | SEQUENCE |
|---|---|---|
| 1 | mecC-MRSA Primer | 5'-TCTTACTATCAAAAAGATTGATAACTCTCGC-3' |
| 2 | mecC-MRSA Primer | 5'-CTCTTTTAGTTTCTATGTACTTTCTTACTATCAA-3' |
| 3 | mecC-MRSA Primer | 5'-GAATATCAAGTAACATCTCAGCAATGATAC-3' |
| 4 | mecC-MRSA Primer | 5'-ATCTGTATAAAATAGATTAGTCCTTTATTGCGTA-3' |
| 5 | mecC-MRSA Primer | 5'-TAGTAAGTGAGGTTGCTGAAATTGTACTA-3' |
| 6 | mecC-MRSA Primer | 5'-CAATTCTCATAAACCTCATACGTAAAGA-3' |
| 7 | mecC-MRSA Primer | 5'-ACGGCAATTCTCATAAACCTCA-3' |
| 8 | mecC-MRSA Primer | 5'-ACTCTCGCAAAACATAACGGC-3' |
| 9 | orfX Primer | 5'-GAAATACAAGGAAAGATGCTATCTTCC-3' |
| 10 | (orfX) mecC MRSA Probe | 5'-TTGAACCAACGCATGACCCAAGGGC-3' |

TABLE II

AMPLICONS

| SEQ ID NO | SEQUENCE |
|---|---|
| 11 | 5'-GAAATACAAGGAAAGATGCTATCTTCCGAAGGATTGGCCCAAGAATTGAAC CAACGCATGACCCAAGGGCAAAGCGACTTTGTATTCGTCATTGGCGGATCAAA TGGCCTGCACAAGGACGTCTTACAACGCAGTAACTACGCACTATCATTCAGCAA AATGACATTTCCACATCAAATGATGCGGGTTGTGTTAATTGAGCAAGTGTATAG AGCGTTTAAGATTATGCGCGGAGAAGCGTATCACAAATGATGCGGTTTTTTTAA CCTCTTTACGTATGAGGTTTATGAGAATTGCCGTTATGTTTTGCGAGAGTTATC AATCTTTTTGATAGTAAGA-3' |

TABLE II-continued

AMPLICONS

| SEQ ID NO | SEQUENCE |
|---|---|
| 12 | 5'-GAAATACAAGGAAAGATGCTATCTTCCGAAGGATTGGCCCAAGAATTGAAC<br>CAACGCATGACCCAAGGGCAAAGCGACTTTGTATTCGTCATTGGCGGATCAAAT<br>GGCCTGCACAAGGACGTCTTACAACGCAGTAACTACGCACTATCATTCAGCAAA<br>ATGACATTTCCACATCAAATGATGCGGGTTGTGTTAATTGAGCAAGTGTATAGA<br>GCGTTTAAGATTATGCGCGGAGAAGCGTATCACAAATGATGCGGTTTTTTTAAC<br>CTCTTTACGTATGAGGTTTATGAGAATTGCCGTTATGTTTTGCGAGAGTTATCA<br>ATCTTTTTGATAGTAAGAAAGTACATAGAAACTAAAAGAG-3' |
| 13 | 5'-GAAATACAAGGAAAGATGCTATCTTCCGAAGGATTGGCCCAAGAATTGAAC<br>CAACGCATGACCCAAGGGCAAAGCGACTTTGTATTCGTCATTGGCGGATCAAAT<br>GGCCTGCACAAGGACGTCTTACAACGCAGTAACTACGCACTATCATTCAGCAAA<br>ATGACATTTCCACATCAAATGATGCGGGTTGTGTTAATTGAGCAAGTGTATAGA<br>GCGTTTAAGATTATGCGCGGAGAAGCGTATCACAAATGATGCGGTTTTTTTAAC<br>CTCTTTACGTATGAGGTTTATGAGAATTGCCGTTATGTTTTGCGAGAGTTATCA<br>ATCTTTTTGATAGTAAGAAAGTACATAGAAACTAAAAGAGTATTTTTATCTACA<br>ATAGCATTTATAATTTATTCTATTATTGTATACTTTATTTTAATTATTAGTATCAT<br>TGCTGAGATGTTACTTGATATTC-3' |
| 14 | 5'-GAAATACAAGGAAAGATGCTATCTTCCGAAGGATTGGCCCAAGAATTGAAC<br>CAACGCATGACCCAAGGGCAAAGCGACTTTGTATTCGTCATTGGCGGATCAAAT<br>GGCCTGCACAAGGACGTCTTACAACGCAGTAACTACGCACTATCATTCAGCAAA<br>ATGACATTTCCACATCAAATGATGCGGGTTGTGTTAATTGAGCAAGTGTATAGA<br>GCGTTTAAGATTATGCGCGGAGAAGCGTATCACAAATGATGCGGTTTTTTTAAC<br>CTCTTTACGTATGAGGTTTATGAGAATTGCCGTTATGTTTTGCGAGAGTTATCA<br>ATCTTTTTGATAGTAAGAAAGTACATAGAAACTAAAAGAGTATTTTTATCTACA<br>ATAGCATTTATAATTTATTCTATTATTGTATACTTTATTTTAATTATTAGTATCAT<br>TGCTGAGATGTTACTTGATATTCTATGTCTATTTTTAGGAAATTCTATACTATT<br>AAAATTATGGTATTTTATACGCAATAAAGGACTAATCTATTTTATACAGAT-3' |
| 15 | 5'-GAAATACAAGGAAAGATGCTATCTTCCGAAGGATTGGCCCAAGAATTGAAC<br>CAACGCATGACCCAAGGGCAAAGCGACTTTGTATTCGTCATTGGCGGATCAAAT<br>GGCCTGCACAAGGACGTCTTACAACGCAGTAACTACGCACTATCATTCAGCAAA<br>ATGACATTTCCACATCAAATGATGCGGGTTGTGTTAATTGAGCAAGTGTATAGA<br>GCGTTTAAGATTATGCGCGGAGAAGCGTATCACAAATGATGCGGTTTTTTTAAC<br>CTCTTTACGTATGAGGTTTATGAGAATTGCCGTTATGTTTTGCGAGAGTTATCA<br>ATCTTTTTGATAGTAAGAAAGTACATAGAAACTAAAAGAGTATTTTTATCTACA<br>ATAGCATTTATAATTTATTCTATTATTGTATACTTTATTTTAATTATTAGTATCAT<br>TGCTGAGATGTTACTTGATATTCTATGTCTATTTTTAGGAAATTCTATACTATT<br>AAAATTATGGTATTTTATACGCAATAAAGGACTAATCTATTTTATACAGATTAG<br>TCCTTTATTGTAGTCTTTAAAAACTAGTTACTCATTAATATTTTTAGTACAATT<br>TCAGCAACCTCACTTACTA-3' |
| 16 | 5'-GAAATACAAGGAAAGATGCTATCTTCCGAAGGATTGGCCCAAGAATTGAAC<br>CAACGCATGACCCAAGGGCAAAGCGACTTTGTATTCGTCATTGGCGGATCAAAT<br>GGCCTGCACAAGGACGTCTTACAACGCAGTAACTACGCACTATCATTCAGCAAA<br>ATGACATTTCCACATCAAATGATGCGGGTTGTGTTAATTGAGCAAGTGTATAGA<br>GCGTTTAAGATTATGCGCGGAGAAGCGTATCACAAATGATGCGGTTTTTTTAAC<br>CTCTTTACGTATGAGGTTTATGAGAATTG-3' |
| 17 | 5'-GAAATACAAGGAAAGATGCTATCTTCCGAAGGATTGGCCCAAGAATTGAAC<br>CAACGCATGACCCAAGGGCAAAGCGACTTTGTATTCGTCATTGGCGGATCAAAT<br>GGCCTGCACAAGGACGTCTTACAACGCAGTAACTACGCACTATCATTCAGCAAA<br>ATGACATTTCCACATCAAATGATGCGGGTTGTGTTAATTGAGCAAGTGTATAGA<br>GCGTTTAAGATTATGCGCGGAGAAGCGTATCACAAATGATGCGGTTTTTTTAAC<br>CTCTTTACGTATGAGGTTTATGAGAATTGCCGT-3' |
| 18 | 5'-GAAATACAAGGAAAGATGCTATCTTCCGAAGGATTGGCCCAAGAATTGAAC<br>CAACGCATGACCCAAGGGCAAAGCGACTTTGTATTCGTCATTGGCGGATCAAAT<br>GGCCTGCACAAGGACGTCTTACAACGCAGTAACTACGCACTATCATTCAGCAAA<br>ATGACATTTCCACATCAAATGATGCGGGTTGTGTTAATTGAGCAAGTGTATAGA<br>GCGTTTAAGATTATGCGCGGAGAAGCGTATCACAAATGATGCGGTTTTTTTAAC<br>CTCTTTACGTATGAGGTTTATGAGAATTGCCGTTATGTTTTGCGAGAGT-3' |

In one embodiment, the above described sets of mecC-MRSA primers and probes are used in order to provide for detection of mecC-MRSA in a biological sample suspected of containing mecC-MRSA. The sets of primers and probes may comprise or consist the primers and probes specific for the mecC-MRSA RE junction nucleic acid sequences, comprising or consisting of the nucleic acid sequences of SEQ ID NOs: 1, 2, 3, 4, 5, 6, 7, 8, 9, and 10. In another embodiment, the primers and probes for the mecC-MRSA targets comprise or consist of a functionally active variant of any of the primers and probes of SEQ ID NOs: 1, 2, 3, 4, 5, 6, 7, 8, 9, and 10.

A functionally active variant of any of the primers and/or probes of SEQ ID NOs: 1, 2, 3, 4, 5, 6, 7, 8, 9, and 10 may be identified by using the primers and/or probes in the disclosed methods. A functionally active variant of a primer and/or probe of any of the SEQ ID NOs: 1, 2, 3, 4, 5, 6, 7, 8, 9, and 10 pertains to a primer and/or probe which provides a similar or higher specificity and sensitivity in the described method or kit as compared to the respective sequence of SEQ ID NOs: 1, 2, 3, 4, 5, 6, 7, 8, 9, and 10.

The variant may, e.g., vary from the sequence of SEQ ID NOs: 1, 2, 3, 4, 5, 6, 7, 8, 9, and 10 by one or more nucleotide additions, deletions or substitutions such as one or more nucleotide additions, deletions or substitutions at the 5' end and/or the 3' end of the respective sequence of SEQ ID NOs: 1, 2, 3, 4, 5, 6, 7, 8, 9, and 10. As detailed above, a primer (and/or probe) may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-desazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify a nucleic acid molecule encoding the mecC-MRSA RE junction nucleic acid sequences, e.g., nucleic acids encoding alternative portions of mecC-MRSA RE junctions can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length).

In addition to a set of primers, the methods may use one or more probes in order to detect the presence or absence of mecC-MRSA. The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids", in the present case to a mecC-MRSA (target) nucleic acid. A "probe" can be referred to as a "detection probe" meaning that it detects the target nucleic acid.

In some embodiments, the described mecC-MRSA probes can be labeled with at least one fluorescent label. In one embodiment, the mecC-MRSA probes can be labeled with a donor fluorescent moiety, e.g., a fluorescent dye, and a corresponding acceptor fluorescent moiety, e.g., a quencher.

In one embodiment, the probe comprises or consists of a fluorescent moiety and the nucleic acid sequences comprise or consist of SEQ ID NO: 10 (shown without the label).

Designing oligonucleotides to be used as probes can be performed in a manner similar to the design of primers. Embodiments may use a single probe or a pair of probes for detection of the amplification product. Depending on the embodiment, the probe(s) use may comprise at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 30 (e.g., 16, 18, 20, 21, 22, 23, 24, or 25) nucleotides in length.

Constructs can include vectors each containing one of mecC-MRSA RE junction primers and probes nucleic acid molecules (e.g., SEQ ID NOs: 1, 2, 3, 4, 5, 6, 7, 8, 9, and 10). Constructs can be used, for example, as control template nucleic acid molecules. Vectors suitable for use are commercially available and/or produced by recombinant nucleic acid technology methods routine in the art. MecC-MRSA nucleic acid molecules can be obtained, for example, by chemical synthesis, direct cloning from mecC-MRSA, or by PCR amplification.

Constructs suitable for use in the methods typically include, in addition to the mecC-MRSA nucleic acid molecules (e.g., a nucleic acid molecule that contains one or more sequences of SEQ ID NOs: 1, 2, 3, 4, 5, 6, 7, 8, 9, and 10), sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs containing mecC-MRSA nucleic acid molecules can be propagated in a host cell. As used herein, the term host cell is meant to include prokaryotes and eukaryotes such as yeast, plant and animal cells. Prokaryotic hosts may include *E. coli*, *Salmonella typhimurium*, *Serratia marcescens*, and *Bacillus subtilis*. Eukaryotic hosts include yeasts such as *S. cerevisiae*, *S. pombe*, *Pichia pastoris*, mammalian cells such as COS cells or Chinese hamster ovary (CHO) cells, insect cells, and plant cells such as *Arabidopsis thaliana* and *Nicotiana tabacum*. A construct can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in some embodiments include oligonucleotides capable of acting as points of initiation of nucleic acid synthesis within the described mecC-MRSA nucleic acid sequences (e.g., SEQ ID NOs: 1, 2, 4, 5, 7, 8, and 9). A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence on the described mecC-MRSA nucleic acid molecules. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

PCR assays can employ mecC-MRSA nucleic acid such as RNA or DNA (cDNA). The template nucleic acid need not be purified; it may be a minor fraction of a complex mixture, such as mecC-MRSA nucleic acid contained in human cells. MecC-MRSA nucleic acid molecules may be extracted from a biological sample by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonucleotide primers (e.g., SEQ ID NOs: 1, 2, 4, 5, 7, 8, and 9) are combined with PCR reagents under reaction conditions that induce primer extension. For example, chain extension reactions generally include 50 mM KCl, 10 mM Tris-HCl (pH 8.3), 15 mM $MgCl_2$, 0.001% (w/v) gelatin, 0.5-1.0 µg denatured template DNA, 50 pmoles of each oligonucleotide primer, 2.5 U of Taq polymerase, and 10% DMSO). The reactions usually contain 150 to 320 µM each of dATP, dCTP, dTTP, dGTP, or one or more analogs thereof.

The newly synthesized strands form a double-stranded molecule that can be used in the succeeding steps of the reaction. The steps of strand separation, annealing, and elongation can be repeated as often as needed to produce the desired quantity of amplification products corresponding to the target mecC-MRSA nucleic acid molecules. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength. In certain systems, non-fluorescent energy can be transferred between donor and acceptor moieties, by way of biomolecules that include substantially non-fluorescent donor moieties (see, for example, U.S. Pat. No. 7,741,467).

In one example, a oligonucleotide probe can contain a donor fluorescent moiety and a corresponding quencher, which may or not be fluorescent, and which dissipates the transferred energy in a form other than light. When the probe is intact, energy transfer typically occurs between the two fluorescent moieties such that fluorescent emission from the donor fluorescent moiety is quenched. During an extension step of a polymerase chain reaction, a probe bound to an amplification product is cleaved by the 5' to 3' nuclease activity of, e.g., a Taq Polymerase such that the fluorescent emission of the donor fluorescent moiety is no longer quenched. Exemplary probes for this purpose are described in, e.g., U.S. Pat. Nos. 5,210,015, 5,994,056, and 6,171,785. Commonly used donor-acceptor pairs include the FAM-TAMRA pair. Commonly used quenchers are DABCYL and TAMRA. Commonly used dark quenchers include Black-Hole Quenchers™ (BHQ), (Biosearch Technologies, Inc., Novato, Calif.), Iowa Black™, (Integrated DNA Tech., Inc., Coralville, Iowa), BlackBerry™ Quencher 650 (BBQ-650), (Berry & Assoc., Dexter, Mich.).

In another example, two oligonucleotide probes, each containing a fluorescent moiety, can hybridize to an amplification product at particular positions determined by the complementarity of the oligonucleotide probes to the mecC-MRSA target nucleic acid sequence. Upon hybridization of the oligonucleotide probes to the amplification product nucleic acid at the appropriate positions, a FRET signal is generated. Hybridization temperatures can range from about 35° C. to about 65° C. for about 10 sec to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorimeter. Excitation to initiate energy transfer, or to allow direct detection of a fluorophore, can be carried out with an argon ion laser, a high intensity mercury (Hg) arc lamp, a fiber optic light source, or other high intensity light source appropriately filtered for excitation in the desired range.

As used herein with respect to donor and corresponding acceptor fluorescent moieties "corresponding" refers to an acceptor fluorescent moiety having an absorbance spectrum that overlaps the emission spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Forster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothiocyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm can be the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety, such as an LC Red 640, can be combined with an oligonucleotide which contains an amino linker (e.g., C6-amino phosphoramidites available from ABI (Foster City, Calif.) or Glen Research (Sterling, Va.)) to produce, for example, LC Red 640-labeled oligonucleotide. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as CX-fluorescein-CPG from BioGenex (San Ramon, Calif.)), or 3'-amino-CPGs that require coupling of a fluorescein-NHS-ester after oligonucleotide synthesis.

Detection of mecC-MRSA

The present disclosure provides methods for detecting the presence or absence of mecC-MRSA in a biological or non-biological sample. Methods provided avoid problems of sample contamination, false negatives, and false positives. The methods include performing at least one cycling step that includes amplifying a portion of mecC-MRSA target nucleic acid molecules from a sample using a plurality of pairs of mecC-MRSA primers, and a FRET detecting step. Multiple cycling steps are performed, preferably in a thermocycler. Methods can be performed using the mecC-MRSA primers and probes to detect the presence of mecC-MRSA, and the detection of mecC-MRSA indicates the presence of mecC-MRSA in the sample.

As described herein, amplification products can be detected using labeled hybridization probes that take advantage of FRET technology. One FRET format utilizes TaqMan® technology to detect the presence or absence of an amplification product, and hence, the presence or absence of mecC-MRSA. TaqMan® technology utilizes one single-stranded hybridization probe labeled with, e.g., one fluorescent dye and one quencher, which may or may not be fluorescent. When a first fluorescent moiety is excited with light of a suitable wavelength, the absorbed energy is transferred to a second fluorescent moiety according to the principles of FRET. The second fluorescent moiety is generally a quencher molecule. During the annealing step of the PCR reaction, the labeled hybridization probe binds to the target DNA (i.e., the amplification product) and is degraded by the 5' to 3' nuclease activity of, e.g., the Taq Polymerase during the subsequent elongation phase. As a result, the fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems) uses TaqMan® technology, and is suitable for performing the methods described herein for detecting the presence or absence of mecC-MRSA in the sample.

Molecular beacons in conjunction with FRET can also be used to detect the presence of an amplification product using the real-time PCR methods. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Another common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler® Instrument. During FRET, the fluorescein transfers its energy to an acceptor fluorescent moiety such as LightCycler®-Red 640 (LC Red 640) or LightCycler®-Red 705 (LC Red 705). The acceptor fluorescent moiety then emits light of a longer wavelength, which is detected by the optical detection system of the LightCycler® instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of mecC-MRSA genomes). If amplification of mecC-MRSA target nucleic acid occurs and an amplification product is produced, the step of hybridizing results in a detectable signal based upon FRET between the members of the pair of probes.

Generally, the presence of FRET indicates the presence of mecC-MRSA in the sample, and the absence of FRET indicates the absence of mecC-MRSA in the sample. Inadequate specimen collection, transportation delays, inappropriate transportation conditions, or use of certain collection swabs (calcium alginate or aluminum shaft) are all conditions that can affect the success and/or accuracy of a test result, however. Using the methods disclosed herein, detection of FRET within, e.g., 45 cycling steps is indicative of an mecC-MRSA infection.

Representative biological samples that can be used in practicing the methods include, but are not limited to dermal swabs, nasal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release mecC-MRSA nucleic acid or in some cases, the biological sample can be contacted directly with the PCR reaction components and the appropriate oligonucleotides.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the mecC-MRSA probes from the mecC-MRSA amplification products can confirm the presence or absence of mecC-MRSA in the sample.

Within each thermocycler run, control samples can be cycled as well. Positive control samples can amplify target nucleic acid control template (other than described amplification products of target genes) using, for example, control primers and control probes. Positive control samples can also amplify, for example, a plasmid construct containing the target nucleic acid molecules. Such a plasmid control can be amplified internally (e.g., within the sample) or in a separate sample run side-by-side with the patients' samples using the same primers and probe as used for detection of the intended target. Such controls are indicators of the success or failure of the amplification, hybridization, and/or FRET reaction. Each thermocycler run can also include a negative control that, for example, lacks target template DNA. Negative control can measure contamination. This ensures that the system and reagents would not give rise to a false positive signal. Therefore, control reactions can readily determine, for example, the ability of primers to anneal with sequence-specificity and to initiate elongation, as well as the ability of probes to hybridize with sequence-specificity and for FRET to occur.

In an embodiment, the methods include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next.

Conventional PCR methods in conjunction with FRET technology can be used to practice the methods. In one embodiment, a LightCycler® instrument is used. The following patent applications describe real-time PCR as used in the LightCycler® technology: WO 97/46707, WO 97/46714, and WO 97/46712.

The LightCycler® can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

As an alternative to FRET, an amplification product can be detected using a double-stranded DNA binding dye such as a fluorescent DNA binding dye (e.g., SYBR® Green or SYBR® Gold (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

It is understood that the embodiments of the present disclosure are not limited by the configuration of one or more commercially available instruments.

Articles of Manufacture/Kits

Embodiments of the present disclosure further provide for articles of manufacture or kits to detect mecC-MRSA. An article of manufacture can include primers and probes used to detect mecC-MRSA, together with suitable packaging materials. Representative primers and probes for detection of mecC-MRSA are capable of hybridizing to mecC-MRSA target nucleic acid molecules. In addition, the kits may also include suitably packaged reagents and materials needed for DNA immobilization, hybridization, and detection, such solid supports, buffers, enzymes, and DNA standards. Methods of designing primers and probes are disclosed herein, and representative examples of primers and probes that amplify and hybridize to mecC-MRSA target nucleic acid molecules are provided.

Articles of manufacture can also include one or more fluorescent moieties for labeling the probes or, alternatively, the probes supplied with the kit can be labeled. For example, an article of manufacture may include a donor and/or an acceptor fluorescent moiety for labeling the mecC-MRSA probes. Examples of suitable FRET donor fluorescent moieties and corresponding acceptor fluorescent moieties are provided above.

Articles of manufacture can also contain a package insert or package label having instructions thereon for using the mecC-MRSA primers and probes to detect mecC-MRSA in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

Embodiments of the present disclosure will be further described in the following examples, which do not limit the scope of the invention described in the claims.

EXAMPLES

The following examples and figures are provided to aid the understanding of the subject matter, the true scope of which is set forth in the appended claims. It is understood that modifications can be made in the procedures set forth without departing from the spirit of the invention.

Example I

MecC-MRSA Gene Targets

Figure 2:
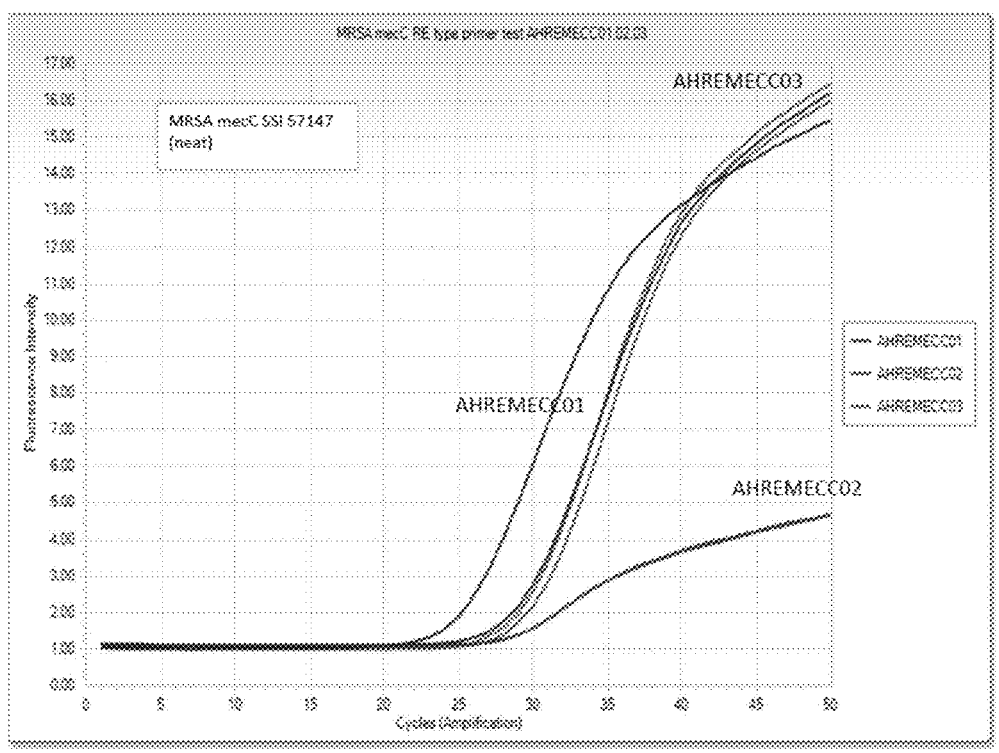
FIG. 2 shows PCR growth curves of experiments using three different primers specific for mecC MRSA. Two primers (AHREMECC01 and AHREMECC03) show similar growth curve performance with respect to fluorescence and elbow value. The third primer (AHREMECC02) had reduced fluorescence and delayed elbow values.
Figure 3:
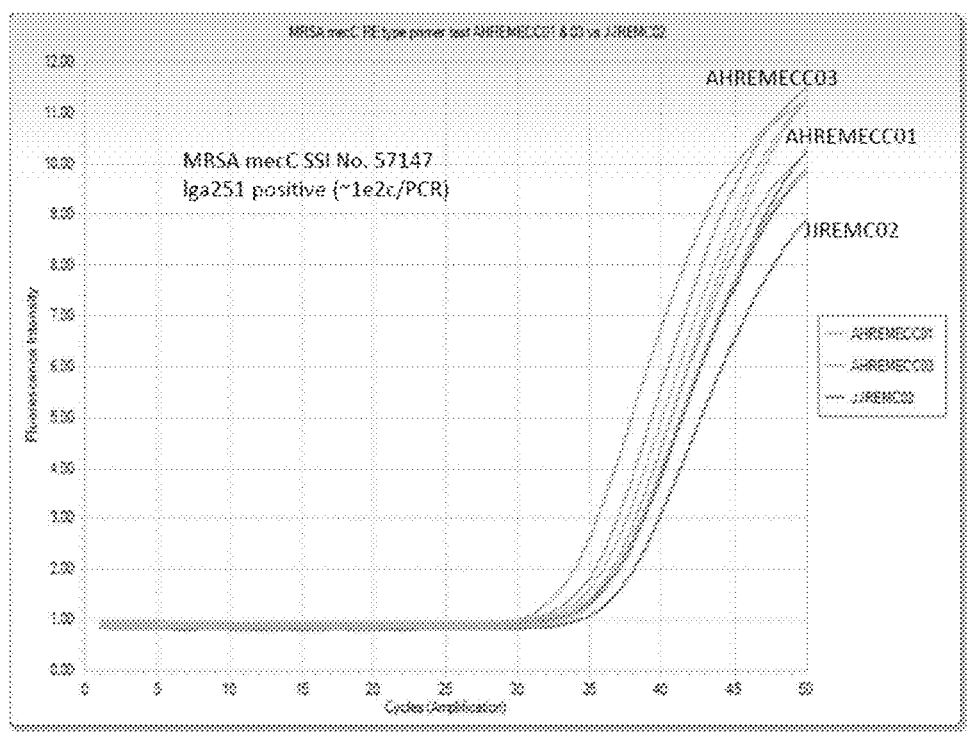
FIG. 3 shows PCR growth curves of experiments using several primers specific for mecC MRSA, all with similar growth curve performance.
Figure 4:
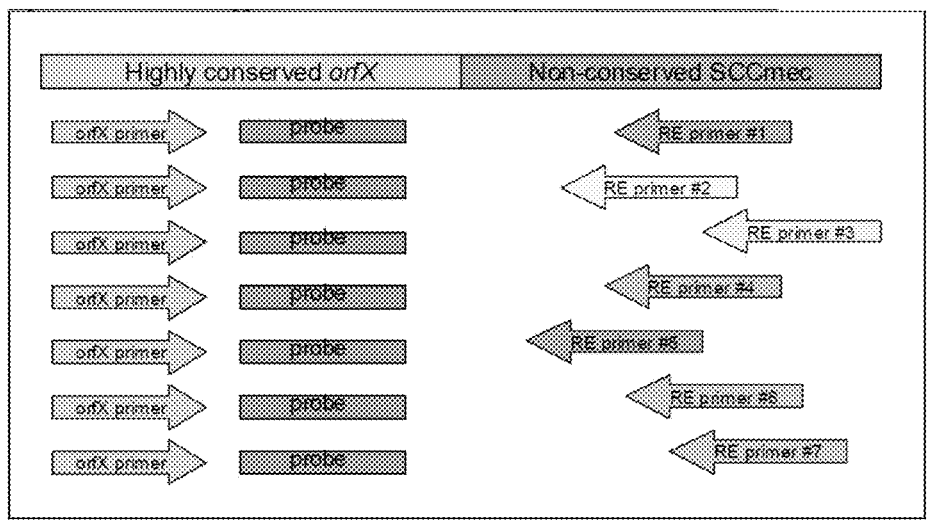
FIG. 4 shows a schematic diagram of MRSA typing based on RE (right extremity of SCCmec) typing.

Referring to FIGS. 1 to 3, the oligo sets #1-8 were evaluated with reference sequence LGA251 Accession No. FR823292.

---
MecC-MRSA Oligo Set #1
---

(SEQ ID NO: 9)
Up Primer: GAAATACAAGGAAAGATGCTATCTTCJ (J = t-butylbenzyl dC)
(SEQ ID NO: 1)
Dn Primer: TCTTACTATCAAAAAGATTGATAACTCTCGJ (J = t-butylbenzyl dC)
(SEQ ID NO: 10)
Probe: ETTGAACQCAACGCATGACCCAAGGGCP (E = thHEX, Q = BHQ2, P = 3' phosphate)

---
Amplicon generated from Oligo Set #1:
---

(SEQ ID NO: 11)
GAAATACAAGGAAAGATGCTATCTTCCGAAGGATTGGCCCAAGAATTGAACCAACGCATGACCCAAGGGCAAAGC

GACTTTGTATTCGTCATTGGCGGATCAAATGGCCTGCACAAGGACGTCTTACAACGCAGTAACTACGCACTATCA

TTCAGCAAAATGACATTTCCACATCAAATGATGCGGGTTGTGTTAATTGAGCAAGTGTATAGAGCGTTTAAGATT

ATGCGCGGAGAAGCGTATCACAAATGATGCGGTTTTTTTAACCTCTTTACGTATGAGGTTTATGAGAATTGCCGT

TATGTTTTGCGAGAGTTATCAATCTTTTTGATAGTAAGA

---
MecC-MRSA Oligo Set #2:
---

(SEQ ID NO: 9)
Up Primer: GAAATACAAGGAAAGATGCTATCTTCJ (J = t-butylbenzyl dC)
(SEQ ID NO: 2)
Dn Primer: CTCTTTTAGTTTCTATGTACTTTCTTACTATCAJ (J = t-butylbenzyl dA)
(SEQ ID NO: 10)
Probe: ETTGAACQCAACGCATGACCCAAGGGCP (E = thHEX, Q = BHQ2, P = 3' phosphate)

---
Amplicon generated from Oligo Set #2:
---

(SEQ ID NO: 12)
GAAATACAAGGAAAGATGCTATCTTCCGAAGGATTGGCCCAAGAATTGAACCAACGCATGACCCAAGGGCAAAGC

GACTTTGTATTCGTCATTGGCGGATCAAATGGCCTGCACAAGGACGTCTTACAACGCAGTAACTACGCACTATCA

TTCAGCAAAATGACATTTCCACATCAAATGATGCGGGTTGTGTTAATTGAGCAAGTGTATAGAGCGTTTAAGATT

ATGCGCGGAGAAGCGTATCACAAATGATGCGGTTTTTTTAACCTCTTTACGTATGAGGTTTATGAGAATTGCCGT

TATGTTTTGCGAGAGTTATCAATCTTTTTGATAGTAAGAAAGTACATAGAAACTAAAAGAG

---
MecC-MRSA Oligo Set #3:
---

(SEQ ID NO: 9)
Up Primer: GAAATACAAGGAAAGATGCTATCTTCJ (J = t-butylbenzyl dA)
(SEQ ID NO: 3)
Dn Primer: GAATATCAAGTAACATCTCAGCAATGATAJ (J = t-butylbenzyl dC)
(SEQ ID NO: 10)
Probe: ETTGAACQCAACGCATGACCCAAGGGCP (E = thHEX, Q = BHQ2, P = 3' phosphate)

---
Amplicon generated from Oligo Set #3:
---

(SEQ ID NO: 13)
GAAATACAAGGAAAGATGCTATCTTCCGAAGGATTGGCCCAAGAATTGAACCAACGCATGACCCAAGGGCAAAGC

GACTTTGTATTCGTCATTGGCGGATCAAATGGCCTGCACAAGGACGTCTTACAACGCAGTAACTACGCACTATCA

-continued

TTCAGCAAAATGACATTTCCACATCAAATGATGCGGGTTGTGTTAATTGAGCAAGTGTATAGAGCGTTTAAGATT

ATGCGCGGAGAAGCGTATCACAAATGATGCGGTTTTTTTAACCTCTTTACGTATGAGGTTTATGAGAATTGCCGT

TATGTTTTGCGAGAGTTATCAATCTTTTTGATAGTAAGAAAGTACATAGAAACTAAAAGAGTATTTTTATCTACA

ATAGCATTTATAATTTATTCTATTATTGTATACTTTATTTTAATTATTA<u>GTATCATTGCTGAGATGTTACTTGAT</u>

<u>ATTC</u>

MecC-MRSA Oligo Set #4:

(SEQ ID NO: 9)
Up Primer: <u>GAAATACAAGGAAAGATGCTATCTTCJ</u> (J = t-butylbenzyl dC)
(SEQ ID NO: 4)
Dn Primer: <u>ATCTGTATAAAATAGATTAGTCCTTTATTGCGTJ</u> (J = t-butylbenzyl dA)
(SEQ ID NO: 10)
Probe: <u>ETTGAACQCAACGCATGACCCAAGGGCP</u> (E = thHEX, Q = BHQ2, P = 3' phosphate)

Amplicon generated from Oligo Set #4:

(SEQ ID NO: 14)
<u>GAAATACAAGGAAAGATGCTATCTTC</u>CGAAGGATTGGCCCAAGAA<u>TTGAACCAACGCATGACCCAAGGGC</u>AAAGC

GACTTTGTATTCGTCATTGGCGGATCAAATGGCCTGCACAAGGACGTCTTACAACGCAGTAACTACGCACTATCA

TTCAGCAAAATGACATTTCCACATCAAATGATGCGGGTTGTGTTAATTGAGCAAGTGTATAGAGCGTTTAAGATT

ATGCGCGGAGAAGCGTATCACAAATGATGCGGTTTTTTTAACCTCTTTACGTATGAGGTTTATGAGAATTGCCGT

TATGTTTTGCGAGAGTTATCAATCTTTTTGATAGTAAGAAAGTACATAGAAACTAAAAGAGTATTTTTATCTACA

ATAGCATTTATAATTTATTCTATTATTGTATACTTTATTTTAATTATTAGTATCATTGCTGAGATGTTACTTGAT

ATTCTATGTCTATTTTTTAGGAAATTCTATACTATTAAAATTATGGTATTTT<u>ATACGCAATAAAGGACTAATCTA</u>

<u>TTTTATACAGAT</u>

MecC-MRSA Oligo Set #5:

(SEQ ID NO: 9)
Up Primer: <u>GAAATACAAGGAAAGATGCTATCTTCJ</u> (J = t-butylbenzyl dC)
(SEQ ID NO: 5)
Dn Primer: <u>TAGTAAGTGAGGTTGCTGAAATTGTACTJ</u> (J = t-butylbenzyl dA)
(SEQ ID NO: 10)
Probe: <u>ETTGAACQCAACGCATGACCCAAGGGCP</u> (E = thHEX (E = thFAM, Q = BHQ2, P = 3'
phosphate)

Amplicon generated from Oligo Set #5:

(SEQ ID NO: 15)
<u>GAAATACAAGGAAAGATGCTATCTTC</u>CGAAGGATTGGCCCAAGAA<u>TTGAACCAACGCATGACCCAAGGGC</u>AAAGC

GACTTTGTATTCGTCATTGGCGGATCAAATGGCCTGCACAAGGACGTCTTACAACGCAGTAACTACGCACTATCA

TTCAGCAAAATGACATTTCCACATCAAATGATGCGGGTTGTGTTAATTGAGCAAGTGTATAGAGCGTTTAAGATT

ATGCGCGGAGAAGCGTATCACAAATGATGCGGTTTTTTTAACCTCTTTACGTATGAGGTTTATGAGAATTGCCGT

TATGTTTTGCGAGAGTTATCAATCTTTTTGATAGTAAGAAAGTACATAGAAACTAAAAGAGTATTTTTATCTACA

ATAGCATTTATAATTTATTCTATTATTGTATACTTTATTTTAATTATTAGTATCATTGCTGAGATGTTACTTGAT

ATTCTATGTCTATTTTTTAGGAAATTCTATACTATTAAAATTATGGTATTTTATACGCAATAAAGGACTAATCTA

TTTTATACAGATTAGTCCTTTATTGTAGTCTTTAAAAACTAGTTACTCATTAATATTTT<u>TAGTACAATTTCAGC</u>

<u>AACCTCACTTACTA</u>

-continued

MecC-MRSA Oligo Set #6:

```
                                                            (SEQ ID NO: 9)
Up Primer: GAAATACAAGGAAAGATGCTATCTTCJ  (J = t-butylbenzyl dC)
                                                            (SEQ ID NO: 6)
Dn Primer: CAATTCTCATAAACCTCATACGTAAAGJ  (J = t-butylbenzyl dA)
                                                            (SEQ ID NO: 10)
Probe: ETTGAACQCAACGCATGACCCAAGGGCP  (E = thHEX, Q = BHQ2, P = 3' phosphate)
```

Amplicon generated from Oligo Set #6:

```
                                                            (SEQ ID NO: 16)
GAAATACAAGGAAAGATGCTATCTTCCGAAGGATTGGCCCAAGAATTGAACCAACGCATGACCCAAGGGCAAAGC

GACTTTGTATTCGTCATTGGCGGATCAAATGGCCTGCACAAGGACGTCTTACAACGCAGTAACTACGCACTATCA

TTCAGCAAAATGACATTTCCACATCAAATGATGCGGGTTGTGTTAATTGAGCAAGTGTATAGAGCGTTTAAGATT

ATGCGCGGAGAAGCGTATCACAAATGATGCGGTTTTTTTAACCTCTTTACGTATGAGGTTTATGAGAATTG
```

MecC-MRSA Oligo Set #7:

```
                                                            (SEQ ID NO: 9)
Up Primer: GAAATACAAGGAAAGATGCTATCTTCJ  (J = t-butylbenzyl dC)
                                                            (SEQ ID NO: 7)
Dn Primer: ACGGCAATTCTCATAAACCTCJ  (J = t-butylbenzyl dA)
                                                            (SEQ ID NO: 10)
Probe: ETTGAACQCAACGCATGACCCAAGGGCP  (E = thHEX, Q = BHQ2, P = 3' phosphate)
```

Amplicon generated from Oligo Set #7:

```
                                                            (SEQ ID NO: 17)
GAAATACAAGGAAAGATGCTATCTTCCGAAGGATTGGCCCAAGAATTGAACCAACGCATGACCCAAGGGCAAAGC

GACTTTGTATTCGTCATTGGCGGATCAAATGGCCTGCACAAGGACGTCTTACAACGCAGTAACTACGCACTATCA

TTCAGCAAAATGACATTTCCACATCAAATGATGCGGGTTGTGTTAATTGAGCAAGTGTATAGAGCGTTTAAGATT

ATGCGCGGAGAAGCGTATCACAAATGATGCGGTTTTTTTAACCTCTTTACGTATGAGGTTTATGAGAATTGCCGT
```

MecC-MRSA Oligo Set #8:

```
                                                            (SEQ ID NO: 9)
Up Primer: GAAATACAAGGAAAGATGCTATCTTCJ  (J = t-butylbenzyl dC)
                                                            (SEQ ID NO: 8)
Dn Primer: ACTCTCGCAAAACATAACGGJ  (J = t-butylbenzyl dC)
                                                            (SEQ ID NO: 10)
Probe: ETTGAACQCAACGCATGACCCAAGGGCP  (E = thHEX, Q = BHQ2, P = 3' phosphate)
```

Amplicon generated from Oligo Set #8:

```
                                                            (SEQ ID NO: 18)
GAAATACAAGGAAAGATGCTATCTTCCGAAGGATTGGCCCAAGAATTGAACCAACGCATGACCCAAGGGCAAAGC

GACTTTGTATTCGTCATTGGCGGATCAAATGGCCTGCACAAGGACGTCTTACAACGCAGTAACTACGCACTATCA

TTCAGCAAAATGACATTTCCACATCAAATGATGCGGGTTGTGTTAATTGAGCAAGTGTATAGAGCGTTTAAGATT

ATGCGCGGAGAAGCGTATCACAAATGATGCGGTTTTTTTAACCTCTTTACGTATGAGGTTTATGAGAATTGCCGT

TATGTTTTGCGAGAGT
```

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A kit for detecting a nucleic acid of mecC-containing methicillin-resistant *Staphylococcus aureus* (mecC-MRSA) comprising:
- a first oligonucleotide consisting of a sequence selected from the group consisting of SEQ ID NOs: 1, 2, 6, and 8;
- a second oligonucleotide configured to hybridize to a portion of an orfX gene, consisting of SEQ ID NO: 9; and
- a detectably labeled third oligonucleotide configured to hybridize to an amplicon generated by the first oligonucleotide and the second oligonucleotide, consisting of SEQ ID NO: 10, or a complement thereof.

2. The kit of claim 1, wherein the detectably labeled third oligonucleotide comprises a donor fluorescent moiety and a corresponding acceptor fluorescent moiety.

3. The kit of claim 2, wherein the acceptor fluorescent moiety is a quencher.

4. The kit of claim 1, further comprising nucleoside triphosphates, nucleic acid polymerase, and buffers necessary for the function of the nucleic acid polymerase.

* * * * *